United States Patent
Chappel

(10) Patent No.: US 10,041,483 B2
(45) Date of Patent: Aug. 7, 2018

(54) METHOD FOR ACCURATE AND LOW-CONSUMPTION MEMS MICROPUMP ACTUATION AND DEVICE FOR CARRYING OUT SAID METHOD

(75) Inventor: Eric Chappel, Versonnex (FR)

(73) Assignee: DEBIOTECH S.A., Lausanne (CH)

( * ) Notice: Subject to any disclaimer, the term of this patent is extended or adjusted under 35 U.S.C. 154(b) by 635 days.

(21) Appl. No.: 14/235,090

(22) PCT Filed: Jul. 27, 2012

(86) PCT No.: PCT/IB2012/053847
§ 371 (c)(1),
(2), (4) Date: Jan. 27, 2014

(87) PCT Pub. No.: WO2013/018011
PCT Pub. Date: Feb. 7, 2013

(65) Prior Publication Data
US 2014/0199181 A1    Jul. 17, 2014

(30) Foreign Application Priority Data

Jul. 29, 2011 (EP) .................................... 11176003

(51) Int. Cl.
*F04B 19/00* (2006.01)
*F04B 43/02* (2006.01)
(Continued)

(52) U.S. Cl.
CPC ....... *F04B 19/006* (2013.01); *A61M 5/14224* (2013.01); *F04B 43/02* (2013.01); *F04B 43/043* (2013.01); *F04B 43/046* (2013.01)

(58) Field of Classification Search
CPC ... A61M 5/14224; F04B 19/006; F04B 43/02; F04B 43/043; F04B 43/046; F04B 49/065
See application file for complete search history.

(56) References Cited

U.S. PATENT DOCUMENTS 4,778,451 A * 10/1988 Kamen ............ A61M 5/16809
128/DIG. 13
5,171,132 A * 12/1992 Miyazaki ............. F04B 43/046
417/322
(Continued)

FOREIGN PATENT DOCUMENTS

EP          1 403 519 A1    3/2004
WO      2010/046728 A1    4/2010
(Continued)

OTHER PUBLICATIONS

Tackett, Herbert H., Jr., James A. Cripe, and Gary Dyson. "Positive Displacement Reciprocating Pump Fundamentals—Power and Direct Acting Types." Twenty Fourth International Pump Users Symposium. Proc. of Pump Users Symposium. N.p.:n.p., 2008. 45-58. Print.*

(Continued)

*Primary Examiner* — Peter J Bertheaud
*Assistant Examiner* — Joseph Herrmann
(74) *Attorney, Agent, or Firm* — Nixon & Vanderhye P.C.

(57) ABSTRACT

The present invention describes the improvements due to alternated actuation cycles to reduce the delivery errors related to the pumping chamber elasticity, the actuator relaxation or hysteresis. The method actuates a pumping device with an optimal driving voltage profile, wherein the pumping device comprises a pumping chamber including a pumping membrane and a voltage controlled actuator connected to said membrane; the movement of said membrane being defined by three positions, namely a rest, a bottom and a top position. The method includes the actuation of the membrane with a pumping pattern including at least two different cycles: Cycle A: rest-bottom-rest-top-rest Cycle B: rest-top-rest-bottom-rest. The invention also relates to a device to carry out the method.

19 Claims, 12 Drawing Sheets

(51) Int. Cl.
*F04B 43/04* (2006.01)
*A61M 5/142* (2006.01)

(56) References Cited

U.S. PATENT DOCUMENTS

| | | | |
|---|---|---|---|
| 9,192,720 B2* | 11/2015 | Chappel | ............ A61M 5/16854 |
| 2004/0115068 A1 | 6/2004 | Hansen et al. | |
| 2006/0097206 A1 | 5/2006 | Eldridge | |
| 2009/0097037 A1 | 4/2009 | Chappel | |
| 2009/0099523 A1 | 4/2009 | Grant et al. | |
| 2011/0142688 A1 | 6/2011 | Chappel et al. | |
| 2014/0199181 A1* | 7/2014 | Chappel | .................. F04B 43/02 417/53 |

FOREIGN PATENT DOCUMENTS

| | | | | |
|---|---|---|---|---|
| WO | WO 2010/046728 A1 | | 4/2010 | |
| WO | WO 2010046728 A1 * | | 4/2010 | ........ A61M 5/16854 |

OTHER PUBLICATIONS

International Preliminary Report on Patentability (IPRP) Chapter I, issued Feb. 4, 2014 for applicant's PCT/IB2012/053847 dated Jul. 27, 2012.

International Search Report for PCT/IB2012/053847, dated Dec. 17, 2013.

Written Opinion of the ISA for PCT/IB2012/053847, dated Dec. 17, 2013.

European Search Report dated Feb. 22, 2012, issued in European Patent Application No. 11176003.

Written Opinion dated Feb. 22, 2012, issued in European Patent Application No. 11176003.9.

English translation of Notice of Reasons for Rejection dated May 31, 2016, issued in Japanese Patent Application No. 2014-522205.

* cited by examiner

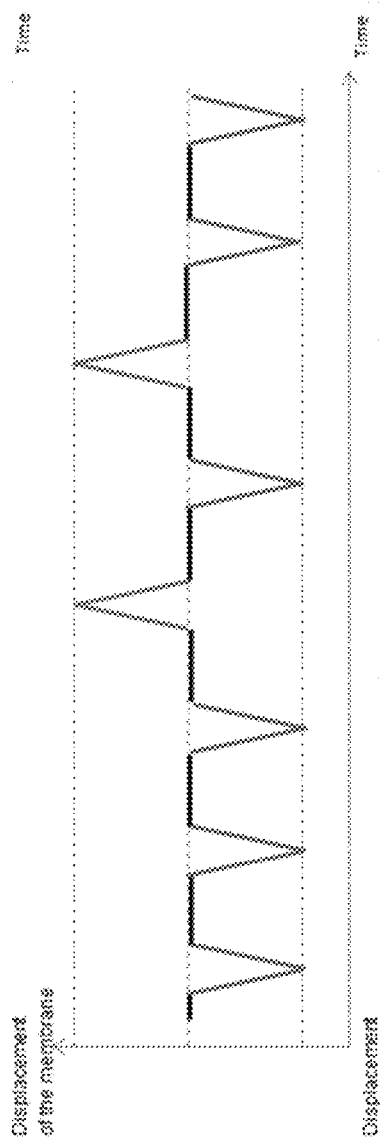
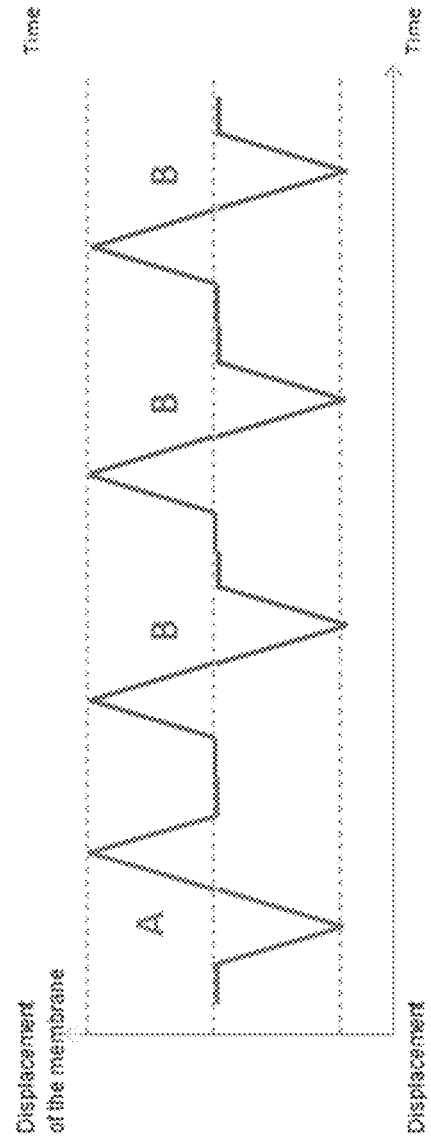
FIG. 7
FIG. 7'

METHOD FOR ACCURATE AND LOW-CONSUMPTION MEMS MICROPUMP ACTUATION AND DEVICE FOR CARRYING OUT SAID METHOD

This application is the U.S. national phase of International Application No. PCT/IB2012/053847 filed 27 Jul. 2012 which designated the U.S. and claims priority to EP Patent Application No. 11176003.9 filed 29 Jul. 2011, the entire contents of each of which are hereby incorporated by reference.

FIELD OF INVENTION

The present invention is related to insulin pumps having a pumping chamber, a pumping membrane and a voltage driven actuator and two valves.

More specifically, the present invention relates to an improved method for accurate and low-consumption actuation profile of membrane micropump, typically for basal infusion of insulin.

PRIOR ART

Reciprocating displacement micropumps have been the subject of an extensive interest. A comprehensive review on the development of microscale devices for pumping fluids has been published by D. J. Laser and J. G. Santiago, J. Micromech. Microeng. 14 (2004) R35-R64. Among these various kinds of devices, the present invention is more specifically related to reciprocating displacement pump having two check valves and a fixed stroke.

The patent application EP 1403519 A1 discloses a membrane pump with stretchable polyimide pump membrane that is moved periodically, using an actuator, between two positions corresponding to a maximum and minimum volume positions where the pump membrane is stretched alternatively against a first and a second wall respectively.

MEMS micropumps are described, for example, in the patent publications US 2006/027523 and WO 2010/046728 A1. This known MEMS micropump 1 as illustrated in FIG. 1 is a highly miniaturized and reciprocating membrane pumping mechanism. It is made from silicon or silicon and glass, using technologies referred to as MEMS (Micro-Electro-Mechanical System). It contains an inlet control member, here an inlet valve 2, a pumping membrane 3, a functional inner detector 4 which allows detection of various failures in the system and an outlet valve 5. The principle of such micro-pumps is known in the prior art, for example from U.S. Pat. No. 5,759,014, the content of which is incorporated by reference in the present application.

FIG. 1 illustrates a micropump with the stack of a glass layer as base plate 8, a silicon layer as second plate 9, secured to the base plate 8, and a second glass layer 10 as a top plate, secured to the silicon plate 9, thereby defining a pumping chamber 11 having a volume.

An actuator (not represented here) linked to the mesa 6 allows the controlled displacement of the pumping membrane 3 between the plates 10 and 8, and more specifically on the anti-bonding layers 21 and 22 (array of tiny square pads on FIGS. 1 and 2) of said plates 10 and 8. Theses plates 10 and 8, having or not anti-bonding layers, are respectively a bottom and a top mechanical stops for the pumping membrane 3. A channel 7 is also present in order to connect the outlet control member, the outlet valve 5 to the outer detector not represented here and finally to the outlet port placed on the opposite side of the pump.

The FIG. 2 illustrates another cross-section of the MEMS micropump including a cover 12 onto the channel 7, an outer detector 13 and a fluidic channel 17 between the outer detector 13 and the outlet port 18.

In the pump 1, the pressure inside the pumping chamber varies during a pumping cycle depending on numerous factors, such as the actuation rate, the pressure at the inlet and the outlet, the potential presence of a bubble volume, the valve characteristics and their leak rates.

Dysfunctions are detected by analysing the pressure profile during actuation cycles.

The inner pressure sensor 4 and outer pressure sensor 13 in the micro-pump 1 are made of a silicon membrane placed between the pumping chamber 11 and the pump outlet 5 and between the pump outlet valve 5 and pump outlet port 18 respectively. The sensors are located in a channel formed between the surface of the micro-pumps silicon layer 9 and its top layer 10. In addition, the sensors comprise a set of strain sensitive resistors in a Wheatstone bridge configuration on the membrane, making use of the huge piezo-resistive effect of the silicon. A change of pressure induces a distortion of the membrane and therefore the bridge is no longer in equilibrium. The sensors are designed to make the signal linear with the pressure within the typical pressure range of the pump. The fluid is in contact with the surface of the interconnection leads and the piezo-resistors. A good electrical insulation of the bridge is ensured by using an additional surface doping of polarity opposite to that of the leads and the piezo-resistors.

During the filling, the mesa pulls the membrane against the bottom mechanical stop; the outlet remains close while the inlet opens when the underpressure in the pumping chamber reaches the inlet valve pretension. During the infusion, the actuator pushes the mesa and therefore the pumping membrane against the upper mechanical stop, inducing an overpressure that opens the outlet valve and maintains the inlet closed.

The device is called a "push-pull" device because the membrane should be pushed to reach the upper stop and pulled to reach the lower stop, its rest position being located more or less at the middle of the stroke, i.e. at the same distance of the two mechanical stops.

The document WO 2010/046728 discloses methods for periodical actuations of a membrane pump, each cycle comprising at least one suction phase and one discharge phase being eventually followed by stationary phases, the pumping chamber volume returning to its initial size at the end of the cycle. The standard single pumping actuation profile as described in WO 2010/046728 is shown FIG. 3. Because maintaining a high voltage onto the piezo actuator electrode is not optimal in terms of power consumption, the stroke is decomposed into a first positive half stroke (hereafter called ½ push), a full negative stroke (full pull or full filling) and finally a second positive half push to complete to actuation cycle. Positive displacement corresponds to an infusion from the pumping chamber toward the patient while negative displacement corresponds to the filling of the pumping chamber from the reservoir.

The nominal single pumping voltage profile is built to ensure that the pumping membrane always reaches the mechanical stops in normal and foreseeable conditions of use.

The pumping chamber has two valves having pretensions, respectively $P_{val\ in}$ for the inlet valve and $P_{val\ out}$ for the outlet valve. During the normal functioning of the pump, the pressure at the end of the pumping cavity filling is negative and equal to $P_{val\ in}$ while at the end of the infusion this pressure becomes positive and equal to $P_{val\ out}$.

In bolus mode, there is a tiny effect of the pumping chamber elasticity on the delivery accuracy because the pumping membrane is moving continuously between the two stop limiters and the pumping membrane is never free to move while the valves are closed.

The pumping membrane is therefore either in movement or against a stop limiter. The maximum volume change in that configuration, when the pressure varies from the valve opening pressure towards zero, is ideally limited to less than 1 nl (detector and outlet valve and membrane volume variation). The elasticity of the system is only increased at the end of the last half stroke of the bolus infusion, when the released membrane is "free".

In basal mode the effect of the pumping chamber elasticity on the delivery accuracy depends on the actuation cycle.

Let us consider the standard actuation cycle made of:
1. an half "push", the membrane moving from its rest position (located between the top and the bottom mechanical stops) towards the top
2. a full "pull", the membrane moving from the top towards the bottom mechanical stops
3. a second half "push", the membrane moving from the bottom towards its rest position During the steps 1 and 2, the effect of the pumping chamber elasticity is limited but during the last half push, because the piezo is no longer powered, the overall elasticity of the pumping chamber is significantly increased by the contribution to the "free" membrane.

The volume change per 100 mbar in the configuration 3 could be up to one or two orders of magnitude larger than in configuration 1 or 2. At the end of a basal stroke, just after the closing of the outlet valve, the membrane could be shifted of several microns from it rest position and the nominal stroke volume is therefore not completely infused. The pressure will therefore release from the pressure $P_{val\ out}$ towards zero in normal conditions of pressure (inlet pressure=outlet pressure=0). During the pressure decay, a residual volume will be infused towards both inlet and outlet via the residual fluidic resistances of the normally "closed" valves.

If the fluidic resistance of the inlet is much larger than the fluidic resistance of the outlet, the effect on the accuracy is negligible: the residual volume will be infused through the outlet and the nominal stroke volume is obtained.

But in the worst case, considering the residual fluidic resistance of the closed inlet is much smaller than the outlet, the residual volume will be infused towards the inlet (backflow), leading to an underinfusion that can be as large as 10% or more of the nominal stroke volume.

Because the ratio between the residual fluidic resistances of the closed valves is purely random, the underinfusion due to the effect discussed above is also purely random.

According to the methods described in the document WO 2010/046728, typical actuation cycles are made of repetition of suction and discharge phases with eventually stationary phases during which the pumping volume does not change, indicating that the pumping membrane is against a stop limiter according during said stationary phases. There is therefore no possibility to have a stationary phase, within a given actuation cycle, when the pumping membrane is for instance in between the two stop limiters.

According to the methods presented in WO 2010/046728 the pumping membrane is forced to perform pumping cycles wherein the pumping membrane moves alternatively between the two stop limiters. But since the actuation cycle is assumed as repetitive, the principle of alternative movement between the two stop limiters is kept during the transition between the end of the cycle and the beginning of the following cycle which will continue the move of the membrane up to the second stop limiter.

All of these methods are conform to the intuitive way to perform pumping cycle with accuracy using a membrane pump having stop limiters: starting from an initial position, reaching alternatively each stop limiter and returning to its original position at the end of the cycle.

There is therefore a need to provide a new actuation profile that makes this random error a systematic error that is not device dependent and that can therefore being compensated.

GENERAL DESCRIPTION OF THE INVENTION

The present invention offers several improvements with respect to state-of-the-art methods.

It refers to a method and a device as defined in the claims.

The object according to the present invention also comprises a MEMS micropump as defined e.g. in US patent application US 2006/027523 and PCT application WO 2010/046728. The contents of those documents are incorporated by reference in the present application Considering reciprocating pumps as described in the state-of-the-art, there is a way to transform the erratic error due to pumping chamber elasticity into a systematic error that can be compensated.

A solution proposed in the present invention is to use a specific pumping pattern that comprise a ½ push (respectively ½ pull) followed by a ½ pull (respectively ½ push). This pumping pattern is not natural for a usual pump and it permits to improve the accuracy of the pump.

In a preferred embodiment, the pumping device comprises a pumping chamber including a pumping membrane and an actuator connected to said membrane. The movement of said membrane is defined by three positions, namely a rest position, a bottom position and a top position; wherein the rest position is comprised between the bottom and the top positions, and wherein said top, rest and bottom positions correspond to a minimum, intermediate and maximum volume of the pumping chamber respectively.

In the preferred embodiment, said pumping pattern comprises alternating at least a ½ push/full pull/½ push cycle with a ½ pull/full push/½ pull cycle, the pumping membrane reaching two times consecutively the same stop limiter during this phase consisting in a partial suction phase followed by a partial discharge phase or vice versa.

By this mean, the pressure at the end of the basal stroke is alternatively positive and negative, inducing a balance of the back-flow every two cycles: the underdelivery becomes systematic and can be compensated.

In another embodiment, the pumping device further comprises an inlet channel which is connected to a reservoir, an outlet channel which is connected to a patient line, a valve located at the inlet channel which has a fluidic resistance named Rin and a valve located at the outlet channel which has a fluidic resistance named Rout. The pumping pattern a ratio $St_{push}/St_{pull}$ which depends of the ratio $R_{in}/R_{out}$, where $St_{push}$ is the number of stop to the rest position preceded by a partial push and $St_{pull}$ is the number of stop to the rest position preceded by a partial pull. Furthermore, if the ratio $R_{in}/R_{out}$ is equal to 1 or unknown, then the ratio $St_{push}/St_{pull}$ must be equal to 1; if the ratio $R_{in}/R_{out}$ is less than 1, then the ratio $St_{push}/St_{pull}$ must be less than 1; if the ratio $R_{in}/R_{out}$ is greater than 1, then the ratio $St_{push}/St_{pull}$ must be greater than 1. This pumping pattern may change over time if the ratio $R_{in}/R_{out}$ changes.

This method, still based on the low consumption concept of WO2010/046728 (the piezo is not powered between each stroke), avoids the random error on the delivery accuracy at basal rate due to the elasticity of the released pumping membrane.

Specific pumping pattern to prevent delivery errors due to actuator relaxation or hysteresis are also proposed in the present invention.

Finally a bolus algorithm is described in order to minimize the delivery error due to the difference between bolus nominal stroke volume and the minimum programmable increment for the bolus volume.

LIST OF FIGURES

Figure 6:
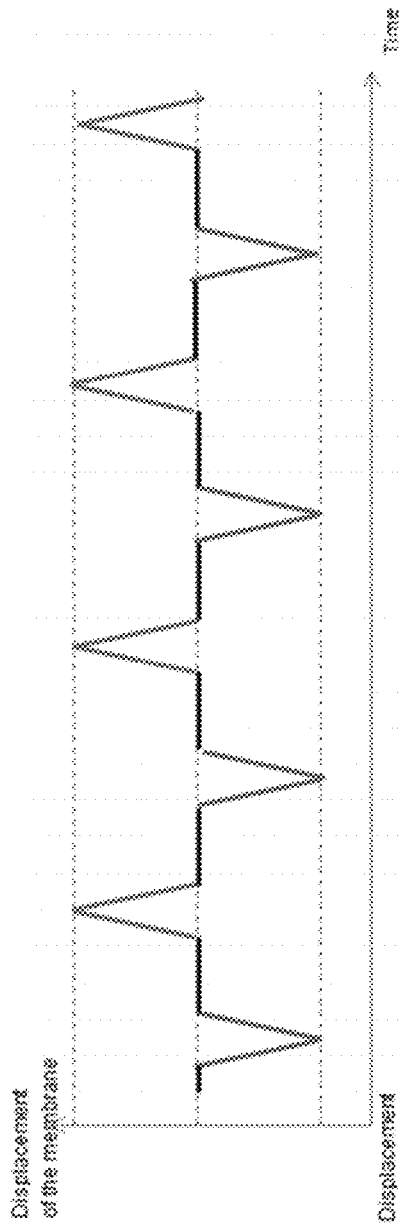
Figure 6:
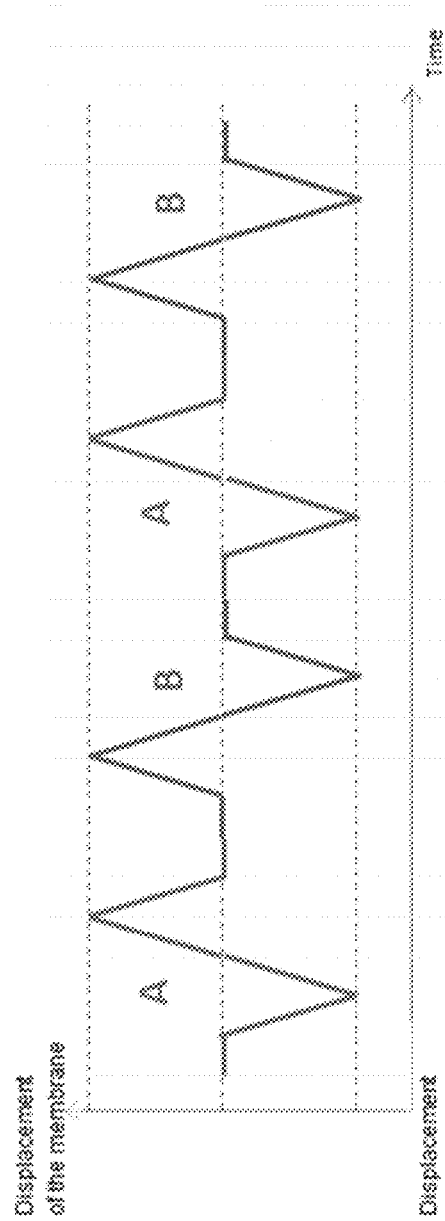
Figure 8:
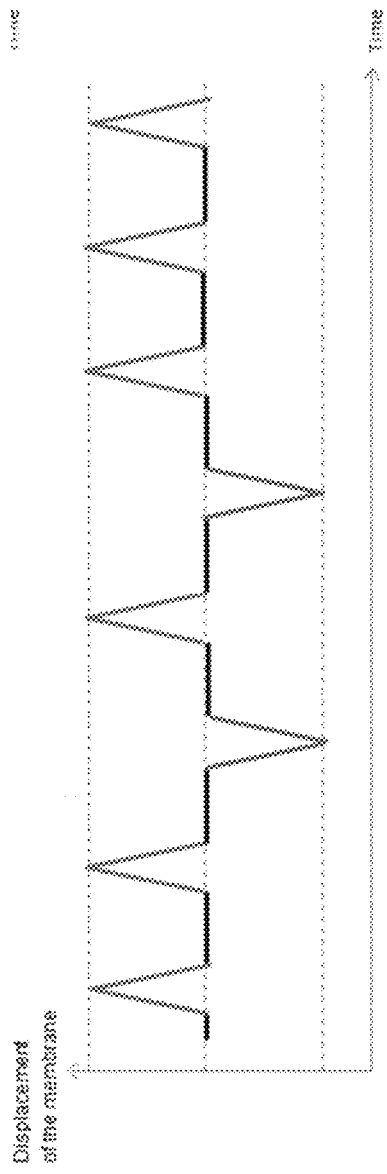
Figure 8:
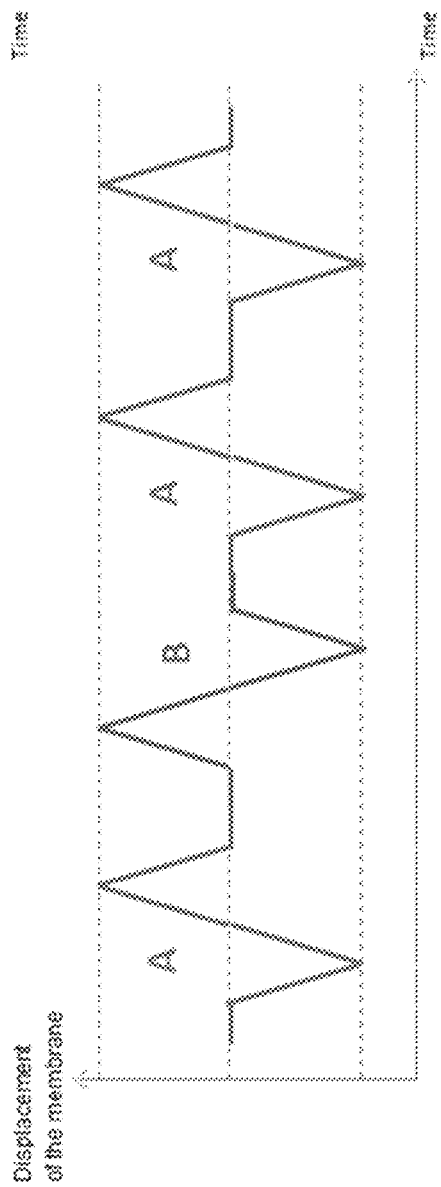
Figure 9:
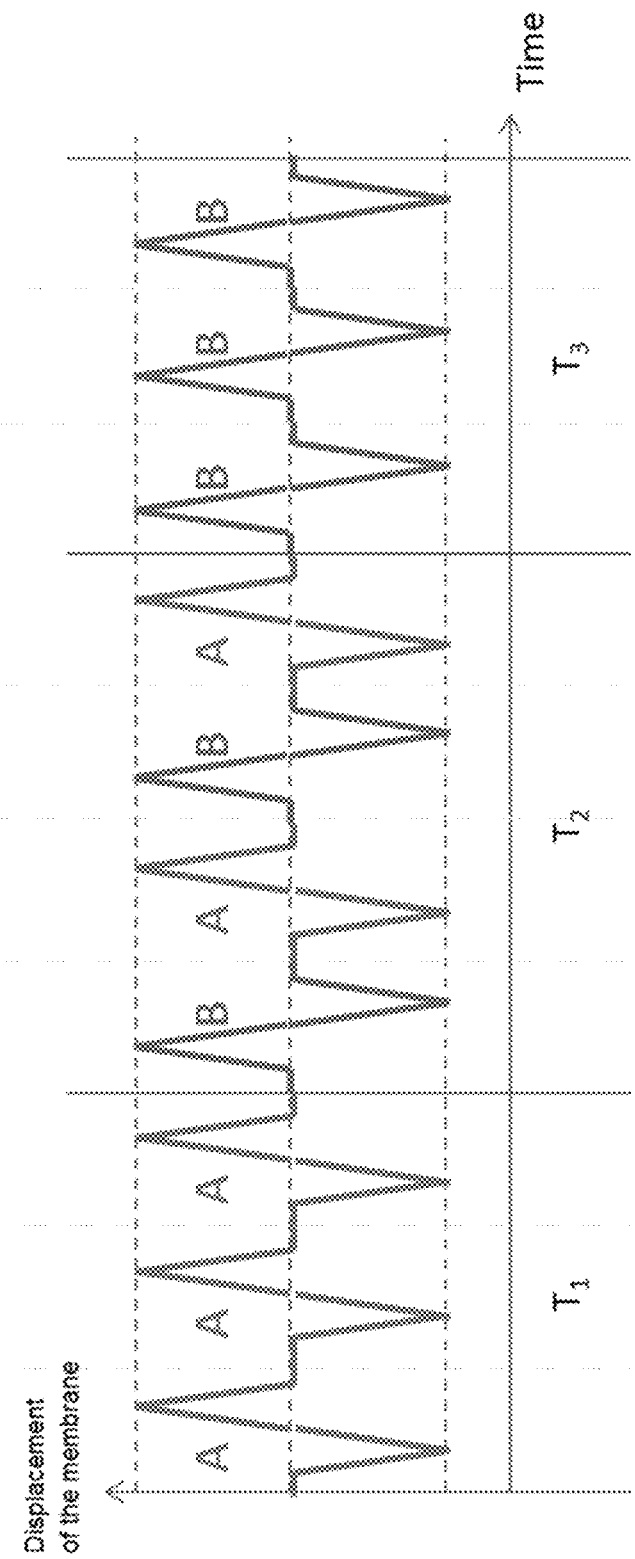
Figure 10:
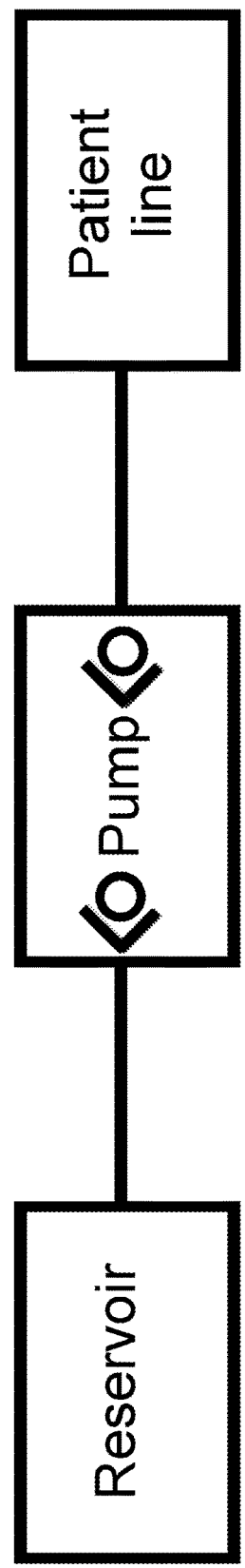

FIGS. 6 and 6' show a pumping pattern which has as much half pull followed by a stop to the rest position as half push followed by a stop to the rest position FIGS. 7 and 7' show a pumping pattern which has less half pull followed by a stop to the rest position than half push followed by a stop to the rest position FIGS. 8 and 8' show a pumping pattern which has more half pull followed by a stop to the rest position than half push followed by a stop to the rest position FIG. 9 shows a pumping pattern which change over time FIG. 10 shows a Reservoir connected to a Pump, having an inlet valve and an outlet valve, connected to a Patient line.

DETAILED DESCRIPTION OF THE INVENTION

Definitions

Stroke

The stroke corresponds here to a full cycle of the pumping membrane, starting from an initial position, reaching iteratively the two mechanical stops and finally coming back to its initial position.

Stroke Volume

Volume change of the pumping cavity, at equilibrium, when the pumping membrane is displaced from the first mechanical stop towards the second mechanical stop.

This stroke volume is the nominal stroke volume or geometrical stroke volume. The stroke volume is equal to the volume injected during a stroke for a pump having valves with opening threshold equal to zero.

The stroke volume is here the minimum volume that can be infused with accuracy.

The volume or the flow rate programmed by the user is decomposed in a sequence of nominal stroke having the required intervals.

Basal and Bolus Stroke Volumes

Effective volume infused during a stroke in basal and bolus mode respectively.

Because the valves have pretensions, the elasticity of the pump has an effect on the effective stroke volume or the volume infused during one stroke. This effect is different in basal and bolus mode.

Single Pumping Voltage Profile

Voltage profile applied to the actuator to perform a single stroke.

The nominal single pumping voltage profile is the basis profile for both standard basal and bolus mode. This nominal single pumping voltage profile is suitable to get the right stroke volume per cycle in normal conditions of temperature and pressure.

Pumping Pattern

Sequence of pumping deliveries.

The pumping unit delivers a pulsed flow rate made of sequence of single pumping like syringe pumps. The intervals between each stroke are adjusted to meet the programmed flow rate and could be regular or irregular.

Back-Flow

Leakage of at least one valve of the pump unit inducing an underdelivery during each stroke even in absence of gradient of pressure between the inlet and the outlet A back flow is typically due to the presence of large particles onto one valve seat and affects both bolus and basal accuracies.

Stationary Phase

A stationary phase is a phase during which the actuator doesn't move substantially. One or more stationary phase may perform between the beginning and the end of the pumping pattern.

For this invention, the stationary phase is characterized by the fact the fluid flows through at least one of said valves even if the both check valves are in closed position.

The stationary phase permits a relaxation of the pressure in the pumping chamber up to an equilibrium pressure. Said relaxation is due to a change of the volume of the fluid present in the pumping chamber induced by a flow through both valves. Where said flow is driven by the difference of pressure between the pumping chamber and both inlet and outlet valves and by the residual fluidic resistances of said valves which are in closed positions. A stop to a position may be a stationary phase.

Rest Position

The rest position is a position of the membrane in the pumping chamber. It is located between the top and the bottom position. Preferably, the rest position is predetermined, non-random and different of top and bottom position.

The rest position and the stationary phase are different. When the pumping pattern performs a full push or a full pull, the membrane moves and goes through said rest position. A stop or a stationary phase at said rest position is possible but not mandatory.

For the present invention, the pumping device comprises a pumping chamber including a pumping membrane and an actuator connected to said membrane, means for actuating the membrane according to a determined pumping pattern, valves which may be a check valves and have a pretension.

In the preferred embodiment, the volume change of the pumping chamber is comprised between 0.5 nl to 50 nl per bar of applied pressure when the pumping membrane is against a mechanical stop, and between 10 nl to 500 nl per bar of applied pressure when the pumping membrane is not against a mechanical stop and when the actuator is not powered.

In one embodiment, the pumping device further comprises a pressure sensor within the pumping chamber and/or means for measuring the fluidic resistance at the inlet and at the outlet or the fluidic resistance difference between the inlet and the outlet.

1.1. Method of Alternated Cycles

In basal mode the effect of the pumping chamber elasticity on the delivery accuracy depends on the pumping pattern.

We consider that the valves (which may be a check valves) have the same opening thresholds in absolute value:

$$-P_{val\ in}=P_{val\ out}=P_{val}$$

Let us consider a first pumping profile (standard single pumping profile or cycle B because the pressure is positive at the end of the actuation) made of:

1. a half "push", the membrane moving from its rest position (located between the top and the bottom mechanical stops) towards the top
2. a full "pull", the membrane moving from the top towards the bottom
3. a second half "push", the membrane being released from the bottom towards its rest position As discussed before, during the steps 1 and 2, the effect of the pumping chamber elasticity is equivalent to the bolus mode with a perfect balancing between the filling (pull) and the infusion (push). But during the last half push, because the piezo is no longer powered, the overall elasticity of the pumping chamber is significantly increased by the contribution to the "free" membrane.

Let us consider now a second pumping profile (cycle A) made of:

4. a half "pull", the membrane moving from its rest position (located between the top and the bottom mechanical stops) towards the bottom
5. a full "push", the membrane moving from the bottom towards the upper mechanical stops
6. a second half "pull", the membrane being release from the bottom towards its rest position We consider $R_{in}$ and $R_{out}$ the fluidic resistances of the inlet and the outlet valves submitted to a gradient of pressure lower than their opening thresholds. We assume these resistances as constant in that range of pressure.

We note $V_r$ the residual volume that will be infused at the end of the basal stroke from the pumping chamber towards both inlet and outlet valves.

If the basal stroke ends by a "push", i.e. a cycle B with a positive pressure in the pumping chamber, the underinfusion is due to an inlet back-flow equal to:

$$V_{r1} = \frac{R_{out}}{R_{in} + R_{out}} V_r$$

This formula shows explicitly that the underinfusion depends on the ratio $R_{in}/R_{out}$.

If the basal stroke ends by a "pull", i.e. a cycle A with a negative pressure in the pumping chamber, the inderinfusion is due to an outlet back-flow equal to:

$$V_{r2} = \frac{R_{in}}{R_{in} + R_{out}} V_r$$

Considering two alternated pumping profiles, i.e. cycle B followed by cycle A or cycle A followed by cycle B, the overall underinfusion is now equal to $V_r$, leading to a mean underinfusion of $V_r/2$ per stroke.

The underinfusion is now systematic and does not depend on the ratio $R_{in}/R_{out}$.

This error can be simply compensated during the calculation of the intervals between the basal strokes.

The cycles A and B presented here are non-limiting examples of the method. Any other cycles including several intermediate positions can be used.

In one embodiment, the pumping pattern includes a number of cycles A which is equal or close to the number of cycles B over a given time interval.

The signal of the pressure sensor in the pumping chamber could be analysed during actuation in order to determine all characteristics necessary to compute the pumping pattern, including the inlet and outlet pressures, the valve pretensions, the stroke completion, the leakage, the presence of air . . . .

In another embodiment showed at the FIG. 6, the pumping pattern includes a stop to the rest position to each half push and half pull.

The FIGS. 6 and 6' show the pumping pattern when the ratio $R_{in}/R_{out}$ is unknown or equal to 1.

So, if the ratio $R_{in}/R_{out}$ is unknown or equal to 1, the pumping pattern must include as much Cycle A as Cycle B or in another word, the pumping pattern must include as much half pull followed by a stop to the rest position as half push followed by a stop to the rest position. It's the same pumping pattern, if a valve leaks but we don't know which one. So if $R_{in}/R_{out}=1$, then $St_{push}/St_{pull}=1$.

The FIGS. 7 and 7' show the pumping pattern when the ratio $R_{in}/R_{out}$ is greater than 1.

So, if the ratio $R_{in}/R_{out}$ is greater than 1, the pumping pattern must include less Cycle A than Cycle B or in another word, the pumping pattern must include less half pull followed by a stop to the rest position than half push followed by a stop to the rest position. It's the same pumping pattern, if the outlet valve leaks. So if $R_{in}/R_{out}>1$, then $St_{push}/St_{pull}>1$ The FIGS. 8 and 8' show the pumping pattern when the ratio $R_{in}/R_{out}$ is less than 1.

So, if the ratio $R_{in}/R_{out}$ is less than 1, the pumping pattern must include more Cycle A than Cycle B or in another word, the pumping pattern must include more half pull followed by a stop to the rest position than half push followed by a stop to the rest position. It's the same pumping pattern, if the inlet valve leaks. So if $R_{in}/R_{out}<1$, then $St_{push}/St_{pull}<1$.

In one embodiment, the pumping device comprises a reservoir. In this case, the pumping pattern may depend of the reservoir level because the fluidic resistance may depend of the reservoir level. So, the FIG. 9 shows three time T1, T2 and T3. When the reservoir is full, $R_{in}/R_{out}$ may be less than 1. Thus, during this time T1, the pumping pattern should include a ratio $St_{push}/St_{pull}<1$ or more Cycle A than Cycle B. But when the reservoir is nearly empty, $R_{in}/R_{out}$ may be greater than 1. Thus, during this time T3, the pumping pattern should include a ratio $St_{push}/St_{pull}>1$ or more Cycle B than Cycle A.

1.2. Detailed Method for Basal Infusion

We provide here a complete calculation of the basal stroke volume including all terms.

Notations:

$P_{val}$=valve pretension or valve opening threshold in absolute value $V_0$=dead volume of the pumping chamber dV=volume change of the pumping chamber, when the membrane is against a mechanical stop, after application of a pressure $P_{val}$
$dV_r$=volume change of the pumping chamber, when the membrane is released (no power on the piezo), after application of a pressure $P_{val}$
$dV_i$=part of the volume dV expulsed through the inlet (i=1) and through the outlet (i=2)
$dV_{ri}$=part of the volume $dV_r$ expulsed through the inlet (i=1) and through the outlet (i=2)
The maxima of $dV_i$ and $dV_{ri}$ take the form (after a complete relaxation of the pumping chamber pressure):

$$\begin{cases} dV_1 = \dfrac{R_{out}}{R_{in} + R_{out}} dV \\ dV_2 = \dfrac{R_{in}}{R_{in} + R_{out}} dV \\ dV_{r1} = \dfrac{R_{out}}{R_{in} + R_{out}} dV_r \\ dV_{r2} = \dfrac{R_{in}}{R_{in} + R_{out}} dV_r \end{cases}$$

We assume that the rest position of the membrane is equidistant from each mechanical stop.

We analyse the volume change for the inlet, the pumping chamber and the outlet at each step of the pumping profile B and pumping profile A for two extreme cases that can occur:

No pressure relaxation except during the release of the membrane (pump very tight)

Full relaxation of the pressure after each move of the membrane (pump safe but at the limit of the specifications in term of tightness)

The volume infused during each step of the basal stroke is estimated as well as the average of two alternate strokes as discussed before.

The tables 1 and 2 summarize the results:

TABLE 1

Volume changes during basal strokes for very tight pumps.

| Pump status | Pchamber | V inlet | Vchamber | V outlet |
|---|---|---|---|---|
| rest position | 0 | 0 | $V_0 + S_V/2$ | 0 |
| ½ push | $+P_{val}$ | 0 | $V_0 + dV$ | $S_V/2 - dV$ |
| Full pull | $-P_{val}$ | $-S_V + 2dV$ | $V_0 + S_V - dV$ | $S_V/2 - dV$ |
| ½ push (release) | $+P_{val}$ | $-S_V + 2dV$ | $V_0 + S_V/2 + dV_r + dV$ | $S_V - 3dV - dV_r$ |
| ½ push (relax) end of cycle B | relax to 0 | $-(S_V - 2dV - dV_1 - dV_{r1})$ | $V_0 + S_V/2$ | $S_V - 2dV - dV_1 - dV_{r1}$ |
| rest position | 0 | 0 | $V_0 + S_V/2$ | 0 |
| ½ pull | $-P_{val}$ | $-S_V/2 + dV$ | $V_0 + S_V - dV$ | 0 |
| Full push | $+P_{val}$ | $-S_V/2 + dV$ | $V_0 + dV$ | $S_V - 2dV$ |
| ½ pull | $-P_{val}$ | $-S_V + 3dV + dV_r$ | $V_0 + S_V/2 - dV_r - dV$ | $S_V - 2dV$ |
| ½ pull (release) end of cycle A | relax to 0 | $-(S_V - 2dV - dV_2 - dV_{r2})$ | $V_0 + S_V/2$ | $S_V - 2dV - dV_2 - dV_{r2}$ |
| average B and A | | $-(S_V - 5dV/2 - dV_r/2)$ | | $S_V - 5dV/2 - dV_r/2$ |

TABLE 2

Volume changes during basal strokes for pumps at the limit of the specifications in term of leakage.

| Pump status | Pchamber | V inlet | Vchamber | V outlet |
|---|---|---|---|---|
| rest position | 0 | 0 | $V_0 + S_V/2$ | 0 |
| ½ push | $+P_{val}$ | 0 | $V_0 + dV$ | $S_V/2 - dV$ |
| ½ push (relax) | relax to 0 | $+dV_1$ | $V_0$ | $S_V/2 - dV + dV_2$ |
| Full pull | $-P_{val}$ | $-(S_V - dV) + dV_1$ | $V_0 + S_V - dV$ | $S_V/2 - dV + dV_2$ |
| Full pull (relax) | relax to 0 | $-S_V + dV$ | $V_0 + S_V$ | $S_V/2 - dV$ |
| ½ push (release) | $+P_{val}$ | $-S_V + dV$ | $V_0 + S_V/2 + dV_r + dV$ | $S_V - 2dV - dV_r$ |
| ½ push (relax) end of cycle B | relax to 0 | $-(S_V - dV - dV_1 - dV_{r1})$ | $V_0 + S_V/2$ | $S_V - dV - dV_1 - dV_{r1}$ |
| rest position | 0 | 0 | $V_0 + S_V/2$ | 0 |
| ½ pull | $-P_{val}$ | $-S_V/2 + dV$ | $V_0 + S_V - dV$ | 0 |
| ½ pull (relax) | relax to 0 | $-S_V/2 + dV_2$ | $V_0 + S_V$ | $-dV_2$ |
| Full push | $+P_{val}$ | $-S_V/2 + dV_2$ | $V_0 + dV$ | $S_V - dV - dV_2$ |
| Full push (relax) | relax to 0 | $-S_V/2 + dV$ | $V_0$ | $S_V - dV$ |
| ½ pull (release) | $-P_{val}$ | $-S_V + 2dV + dV_r$ | $V_0 + S_V/2 - dV_r - dV$ | $S_V - dV$ |
| ½ pull (relax) end of cycle A | relax to 0 | $-(S_V - dV - dV_2 - dV_{r2})$ | $V_0 + S_V/2$ | $S_V - dV - dV_2 - dV_{r2}$ |
| average B and A | | $-(S_V - 3dV/2 - dV_r/2)$ | | $S_V - 3dV/2 - dV_r/2$ |

A sketch of the pump under actuation is provided in the table 3 for the cycle B wherein a total pressure relaxation takes place after each actuation step. To illustrate the effect of elasticity we represent here the detector membrane that is deflected downwardly (resp. upwardly) for positive (resp. negative) pressure in the pumping chamber. The directions of the flows are represented at each step of the cycle by large black arrows.

TABLE 3

Illustrative view showing the direction of the flows (large black arrows) during a cycle B.

| Pump status | cycle B | | Pchamber |
|---|---|---|---|
| rest position | Inlet | outlet | 0 |
| 1/2 push | pumping membrane → SV/2 - dV; P > 0; ↑ detector membrane | | +Pval |
| 1/2 push (relax) | dV1 ← → dV2 | | relax to 0 |
| Full pull | SV- → ; P < 0; ↓ | | -Pval |
| Full pull (relax) | dV1 → ← dV2 | | relax to 0 |
| 1/2 push (release) | → SV/2 - dVr - dV | | +Pval |
| 1/2 push (relax) | dV1 + dVr1 ← → dV2 + dVr2 | | relax to 0 |

In table 4, the same illustrative sketch is provided for the cycle A.

TABLE 4

Illustrative view showing the direction of the flows (large black arrows) during a cycle A.

| Pump status | cycle A | | Pchamber |
|---|---|---|---|
| rest position | Inlet | outlet | 0 |
| 1/2 pull | SV/2- → ; detector membrane; P < 0; ↓ pumping membrane | | -Pval |
| 1/2 pull (relax) | dV1 → ← dV2 | | relax to 0 |
| Full push | → SV-dV; P > 0; ↑ | | +Pval |

TABLE 4-continued

Illustrative view showing the direction of the flows (large black arrows) during a cycle A.

| Pump status | cycle A | | Pchamber |
|---|---|---|---|
| Full push (relax) | dV1 ← → dV2 | | relax to 0 |
| 1/2 pull (release) | SV/2 - dVr - dV → | | -Pval |
| 1/2 pull (relax) | dV1 + dVr1 → ← dV2 + dVr2 | | relax to 0 |

According to the method described here above, the average stroke volume for two alternated cycles B and A only depend on dV and $dV_r$ but not on the ratio $R_{in}$ over $R_{out}$.

Basal Stroke Volume with Alternate Cycles

The basal stroke volume finally takes the form, using alternated pumping profiles:

$$S_v(\text{alternate basal}) = S_v - \frac{dV_r}{2} - 2dV \pm \frac{dV}{2}$$

Example
dV=0.48 nl
$dV_r$=8.28 nl

We obtain an error of +/−0.24 nl.

We consider now the residual error due to the tolerance on the valve pretensions.

This residual error is based on a tolerance of 20% at 3 sigma (target 10%).

Because dV and $dV_r$ vary linearly with the valve pretensions, we obtain finally:

error(alternate basal stroke)=±1.26 nl

The residual error of +/−1.26 nl due to the elasticity cannot be compensated except by measuring the valve pretension with accuracy during the pump functioning.

It is important to note that the compensation of the elasticity effect on accuracy by using alternate strokes is not valid at high flow rate (more than 10 U/h or 0.1 ml/h for U100 insulin) because the pressure may not relax completely between each stroke.

Basal Stroke Volume without Alternate Cycles (Standard Cycle)

$$S_v(\text{standard basal}) = S_v - dV - dV_1 - dV_{r1} = S_v - dV - \frac{dV + dV_r}{2} \pm \frac{dV + dV_r}{2}$$

We obtain an error of +/−4.38 nl.

The residual error on the valve pretension leads to the final value of the standard basal stroke volume:

error standard basal stroke)=±5.35 nl

The error due to the elasticity of the pump is here +/−5.35 nl.

1.3. Detailed Method to Compensate Piezo Hysteresis

Piezo actuators driven in open loop show hysteresis and relaxation. Because the actuator is overdriven against the mechanical stops, the single effect of hysteresis and relaxation is met during the release of the actuator and more especially using alternated pumping profiles B and A.

When the pumping profile ends by a ½ pull (resp. a ½ push), the rest position of the membrane is slightly shifted from the initial neutral position due to piezo hysteresis and relaxation. This shift strongly depends on the interval duration between strokes. To simplify, the difference between the rest positions of the membrane after pumping profiles B and A is called hereafter hysteresis.

Once the electrodes are short-circuited, PZT piezo bimorphs show typically a total hysteresis of 0.8 um after 30 seconds, 0.5 um after 60 seconds and only 0.1 um after 5 minutes.

Below 0.5 U/h the effect is negligible.

At higher basal rate, there is two ways to compensate the effect of hysteresis and relaxation of the piezo for alternated pumping profiles:

1. compensation=change of the basal stroke volume
2. specific pumping cycle=reduction of the number of consecutive alternate cycles Compensation Method The volume infused during each step of the basal stroke is estimated as well as the average of two alternated pumping profiles as discussed before.

We note h the ratio between the total hysteresis and the stroke in %.

The tables 5 and 6 summarize the results.

At 1.2 U/h, for a cycle B followed by a cycle A or a cycle A followed by a cycle B, the mean stroke volume reduction for the two consecutive strokes is equal to 1% or 2 nl. Because this error is systematic the nominal stroke volume can be adjusted to compensate the hysteresis effect.

We suppose a max variation of 20% on the effect of hysteresis for different batches of piezo.

The final error on the stroke volume using alternate cycle with compensation of both elasticity and hysteresis become, at 1.2 U/h:

error(alternate basal stroke)=±1.66 nl

The effective stroke volume is reduced of 2 nl.

The compensation should be calculated for each basal rate larger than 0.5 U/h.

The flow rate and error estimation given here are non-limiting examples of the method.

Specific Pumping Cycle Method

Hysteresis or relaxation changes the stroke volume only for two consecutive alternate actuations at moderate or high basal rate.

To reduce the effect of hysteresis/relaxation, the method comprises not alternating each time a cycle B with a cycle A but to perform Y cycles B followed by Y cycles A. The mean effect due to the hysteresis is divided by a factor Y.

TABLE 5

Volume changes during basal strokes for very tight pumps.

| Pump status | Pchamber | V inlet | Vchamber | V outlet |
| --- | --- | --- | --- | --- |
| rest position A | 0 | 0 | $V0 + SV(1 - h)/2$ | 0 |
| ½ push | $+P_{val}$ | 0 | $V0 + dV$ | $SV(1 - h)/2 - dV$ |
| Full pull | $-P_{val}$ | $-SV + 2dV$ | $V0 + SV - dV$ | $SV(1 - h)/2 - dV$ |
| ½ push (release) | $+P_{val}$ | $-SV + 2dV$ | $V0 + SV(1 + h)/2 + dVr + dV$ | $SV(1 - h) - 3dV - dVr$ |
| ½ push (relax) end of cycle B | relax to 0 | $-(SV - 2dV - dV1 - dVr1)$ | $V0 + SV(1 + h)/2$ | $SV(1 - h) - 2dV - dV1 - dVr1$ |
| rest position B | 0 | 0 | $V0 + SV(1 + h)/2$ | 0 |
| ½ pull | $-P_{val}$ | $-SV(1 - h)/2 + dV$ | $V0 + SV - dV$ | 0 |
| Full push | $+P_{val}$ | $-SV(1 - h)/2 + dV$ | $V0 + dV$ | $SV - 2dV$ |
| ½ pull | $-P_{val}$ | $-SV(1 - h) + 3dV + dVr$ | $V0 + SV(1 - h)/2 - dVr - dV$ | $SV - 2dV$ |
| ½ pull (release) end of cycle A | relax to 0 | $-(SV(1 - h) - 2dV - dV2 - dVr2)$ | $V0 + SV/2$ | $SV - 2dV - dV2 - dVr2$ |
| average B and A | | $-(SV(1 - h/2) - 5dV/2 - dVr/2)$ | | $SV(1 - h/2) - 5dV/2 - dVr/2$ |

TABLE 6

Volume changes during basal strokes for pumps at the limit of the specifications in term of leakage.

| Pump status | Pchamber | V inlet | Vchamber | V outlet |
| --- | --- | --- | --- | --- |
| rest position A | 0 | 0 | $V0 + SV(1 - h)/2$ | 0 |
| ½ push | $+P_{val}$ | 0 | $V0 + dV$ | $SV(1 - h)/2 - dV$ |
| ½ push (relax) | relax to 0 | $+dV1$ | $V0$ | $SV(1 - h)/2 - dV + dV2$ |
| Full pull | $-P_{val}$ | $-(SV - dV) + dV1$ | $V0 + SV - dV$ | $SV(1 - h)/2 - dV + dV2$ |
| Full pull (relax) | relax to 0 | $-SV + dV$ | $V0 + SV$ | $SV(1 - h)/2 - dV$ |
| ½ push (release) | $+P_{val}$ | $-SV + dV$ | $V0 + SV(1 + h)/2 + dVr + dV$ | $SV(1 - h) - 2dV - dVr$ |
| ½ push (relax) end of cycle B | relax to 0 | $-(SV - dV - dV1 - dVr1)$ | $V0 + SV(1 + h)/2$ | $SV(1 - h) - dV - dV1 - dVr1$ |
| rest position B | 0 | 0 | $V0 + SV(1 + h)/2$ | 0 |
| ½ pull | $-P_{val}$ | $-SV(1 - h)/2 + dV$ | $V0 + SV - dV$ | 0 |
| ½ pull (relax) | relax to 0 | $-SV(1 - h)/2 + dV2$ | $V0 + SV$ | $-dV2$ |
| Full push | $+P_{val}$ | $-SV(1 - h)/2 + dV2$ | $V0 + dV$ | $SV - dV - dV2$ |
| Full push (relax) | relax to 0 | $-SV(1 - h)/2 + dV$ | $V0$ | $SV - dV$ |
| ½ pull (release) | $-P_{val}$ | $-SV(1 - h) + 2dV + dVr$ | $V0 + SV(1 - h)/2 - dVr - dV$ | $SV - dV$ |
| ½ pull (relax) end of cycle A | relax to 0 | $-(SV(1 - h) - dV - dV2 - dVr2)$ | $V0 + SV(1 - h)/2$ | $SV - dV - dV2 - dVr2$ |
| average B and A | | $-(SV(1 - h/2) - 3dV/2 - dVr/2)$ | | $SV(1 - h/2) - 3dV/2 - dVr/2$ |

At 2.4 U/h, using a pumping cycle made of 5 cycles B followed by 5 cycles A, the effect of the hysteresis is equal to a mean reduction of the stroke volume equal to (0.5*0.8*200.64)/24.75/5=0.64 nl.

The accuracy error due to elasticity and piezo hysteresis becomes:

error(alternate basal stroke)=±1.39 nl

Increasing the number Y of cycles reduces the relative error due to hysteresis and relaxation.

This actuation profile is suitable to compensate the effect of elasticity and to make the effect of hysteresis negligible.

The method is not limited to the use of a piezo actuator but includes SMA, electromagnetic, capacitive, magnetic, magnetostrictive or any other actuators.

1.4. Other Methods

Any other cycles C, D . . . including several intermediate positions can be used for all of these methods. The numbers N, of cycles i, where i=A, B, C . . . , may be different between each others.

As non-limiting example, the cycle C could be a simple time interval without any actuation.

A cycle may be a simple half positive and negative stroke from the rest position of the membrane towards a top and a bottom positions respectively.

Considering the cycles A and B, non-limiting examples are given below:
ABABAB . . .
AABBAABB . . .
A . . . AB . . . BA . . . AB . . . B . . .
ABAABABABBAB . . .
AB . . . BAB . . . BAB . . . BA . . .
A . . . ABA . . . ABA . . . AB . . .
. . .

Considering the additional cycle C, we can actuate the pumping membrane according to:
ABCABCABC . . .
AB . . . BCA . . . ABA . . . ABC . . .
A . . . AB . . . BC . . . CA . . . AB . . . BC . . . C . . .
ABCBABCBA . . .
ABCBACABCBAC . . .
ABACBABACBA . . .
AB . . . BC . . . CAB . . . BC . . . C . . .
ABC . . . C ABC . . . CABC . . . C . . .
A . . . AB . . . BCA . . . AB . . . BC . . .
A . . . ABC . . . CA . . . ABC . . . C . . .
AB . . . BC . . . CAB . . . BC . . . CAB . . . BC . . . C
. . .

The time periodicity is not mandatory: any of the preceding examples of pumping pattern can have a time interval between strokes that is not constant. The perfect periodicity in term of type of cycles is no longer mandatory: e.g. the algorithm that defines the pumping pattern can use any input or trigger, e.g. the pumping pattern should for instance simply ensure that the overall number N, of cycles i is more or less within the target for a predefined time interval. In practice a counter can be used to that end.

The pumping device includes any processing means including hardware (processors), embedded software . . . to compute and determine the pumping pattern according to the methods described in the present invention.

Pumping pattern may comprise preferably (or only) cycles A or cycles B if the probability to get permanent opening or particles on one specific valve by contrast to the other one is large: according to the flow direction, the inlet valve may have a higher probability to be submitted first to particles coming from the reservoir. In the latter case, as an alternative to the method described previously, the pumping pattern could comprise only cycles of type A which end by a half filling of the pumping chamber, the relative pressure in the pumping chamber being therefore negative after the cycle completion. Once the inlet valve closes, the residual flow that takes place to equilibrate the pressures will mainly occur between the reservoir and the pumping chamber, the back-flow through the outlet valve being small, and thus the effective stroke volume is expected to be very close to the nominal stroke volume.

In case of a higher probability to get particles or permanent opening on the outlet valve, pumping cycles made preferably or only of cycles B should be preferred.

To summarize, if by design or process considerations the probability to have a residual fluidic resistance of the outlet (resp. inlet) valve larger than the residual fluidic resistance of the inlet (resp. outlet) valve is high (close to 1), the pumping pattern should comprise preferably (or only) cycles of A (resp. B) type. In another word, if there is a leakage at the inlet (resp. outlet), the pumping pattern should comprise preferably (or only) cycles of A (resp. B) type.

This method is an approximation of the complete method based on the use of alternated cycles as described previously. This alternative method is however simpler in term of software development since the detection algorithms should be implemented for either cycles A or cycles B while for the complete method the detection algorithms for both kinds of cycles A and B shall be implemented.

Moreover, since this method is based on the use of a single kind of actuation cycles A or B, it is no longer necessary to compensate piezo hysteresis effect as varies the actuation frequency, leading again to simpler delivery algorithms.

1.5. Detailed Method for Bolus Infusion

Pumping Chamber Elasticity and Bolus Stroke Volume

We analyse the volume change at the inlet, the pumping chamber and the outlet during each step of the bolus pumping profile, making a complete cycle from an initial position against one mechanical stop, and considering two extreme cases:
No pressure relaxation except during the release of the membrane at the end of the bolus (=pump very tight)
Full relaxation of the pressure after each move of the membrane (=pump safe but at the limit of the specifications in term of tightness)

The volume infused during each step of the bolus stroke is estimated.

The tables 7 and 8 summarize the results.

TABLE 7

Volume changes during bolus strokes for very tight pumps.

| Pump status | Pchamber | V inlet | Vchamber | V outlet |
|---|---|---|---|---|
| Full pull (ref) | $-P_{val}$ | 0 | $V_0 + S_V - dV$ | 0 |
| Full push | $+P_{val}$ | 0 | $V_0 + dV$ | $S_V - 2dV$ |
| Full pull | $-P_{val}$ | $S_V - 2dV$ | $V_0 + S_V - dV$ | $S_V - 2dV$ |

TABLE 8

Volume changes during bolus strokes for pumps at the limit of the specifications in term of leakage.

| Pump status | Pchamber | V inlet | Vchamber | V outlet |
|---|---|---|---|---|
| Full pull (ref) | $-P_{val}$ | 0 | $V_0 + S_V - dV$ | 0 |
| Full pull (relax) | 0 | $-dV_1$ | $V_0 + S_V$ | $-dV_2$ |

TABLE 8-continued

Volume changes during bolus strokes for pumps at the limit of the specifications in term of leakage.

| Pump status | Pchamber | V inlet | Vchamber | V outlet |
|---|---|---|---|---|
| Full push | $+P_{val}$ | $-dV_1$ | $V_0 + dV$ | $S_V - dV - dV_2$ |
| Full push (relax) | 0 | 0 | $V_0$ | $S_V - dV$ |
| Full pull | $-P_{val}$ | $S_V - dV$ | $V_0 + S_V - dV$ | $S_V - dV$ |

We obtain:

$$S_v(\text{bolus}) = S_v - \frac{3dV}{2} \pm \frac{dV}{2}$$

Finally, considering the tolerance of 20% on the valve pretension, we obtain a typical infusion error due to elasticity equal to:

error(bolus stroke)=±0.384 nl

During the last half stroke at the end of the bolus infusion which corresponds for instance to the release of the membrane from the bottom to the rest position, there is a max punctual error of few nl due to the elasticity of the "free" membrane as discussed for basal infusion.

Bolus Delivery Algorithm

In bolus mode, the patient programs a volume of insulin $V_{bolus}$ to be infused within a short period. The volume $V_{bolus}$ varies typically from 0 to 25 U with typical steps of 0.02 U.

According to the method described above for basal delivery, it could be useful to adjust by design the nominal basal stroke volume to a multiple of the minimum increment of the infused volume that can be programmed every hour and/or the minimum increment for a bolus volume.

In this latter case, the bolus stroke volume will not be a perfect multiple of said minimum programmable increment (for instance 0.02 U), and a bolus delivery algorithm should be implemented to calculate the number of bolus stroke to be delivered.

The Pump Controller divides $V_{bolus}$ by the nominal bolus stroke volume:

$$n = \frac{V_{bolus}}{S_v(\text{bolus})}$$

The number of stroke N to be delivered is simply the integer nearest of n.

We note $\lfloor n \rfloor$ the floor (or integer part) of n, respectively the largest integer not greater than n.

If $n - \lfloor n \rfloor > 0.5$, then $N = \lfloor n \rfloor + 1$

If $n - \lfloor n \rfloor \leq 0.5$, then $N = \lfloor n \rfloor$

Figure 1:
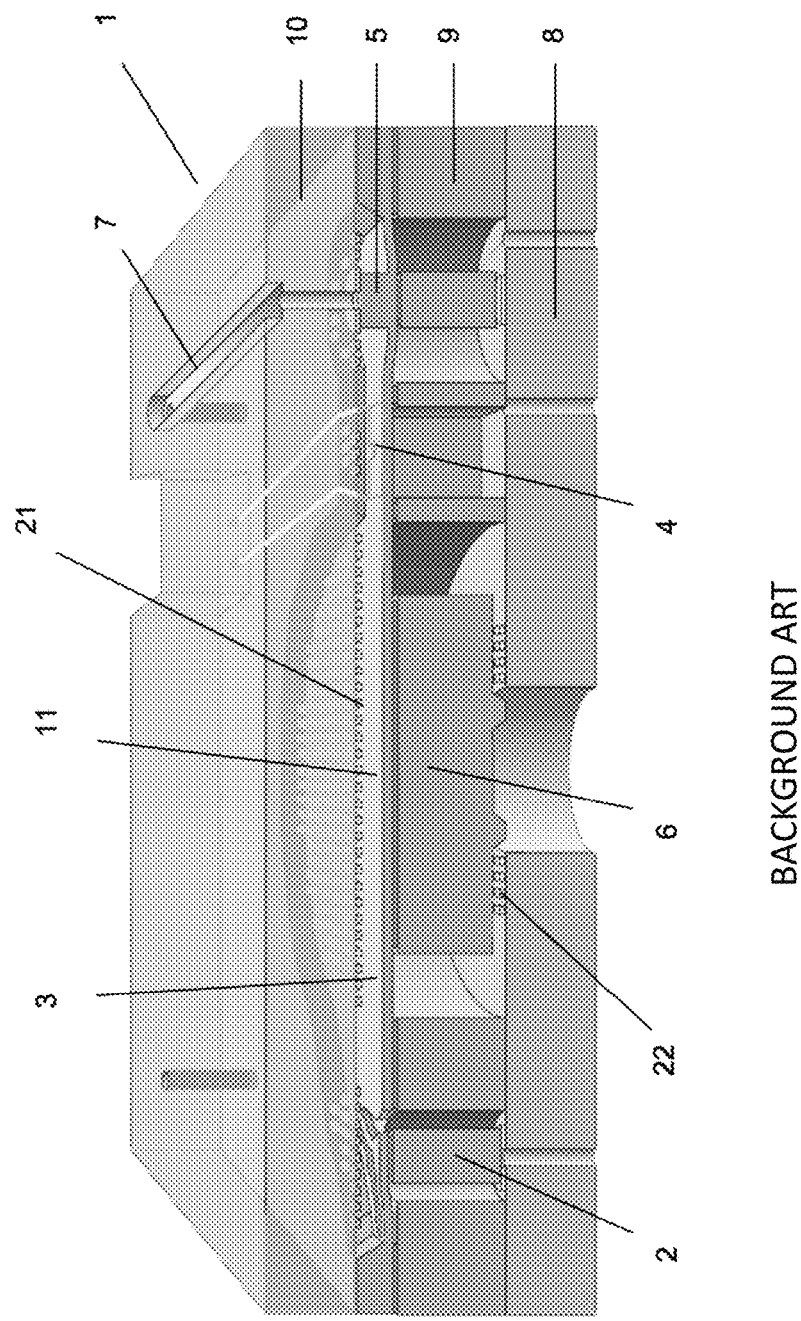
FIG. 1 is a cross-section of the MEMS micropump
Figure 1A:
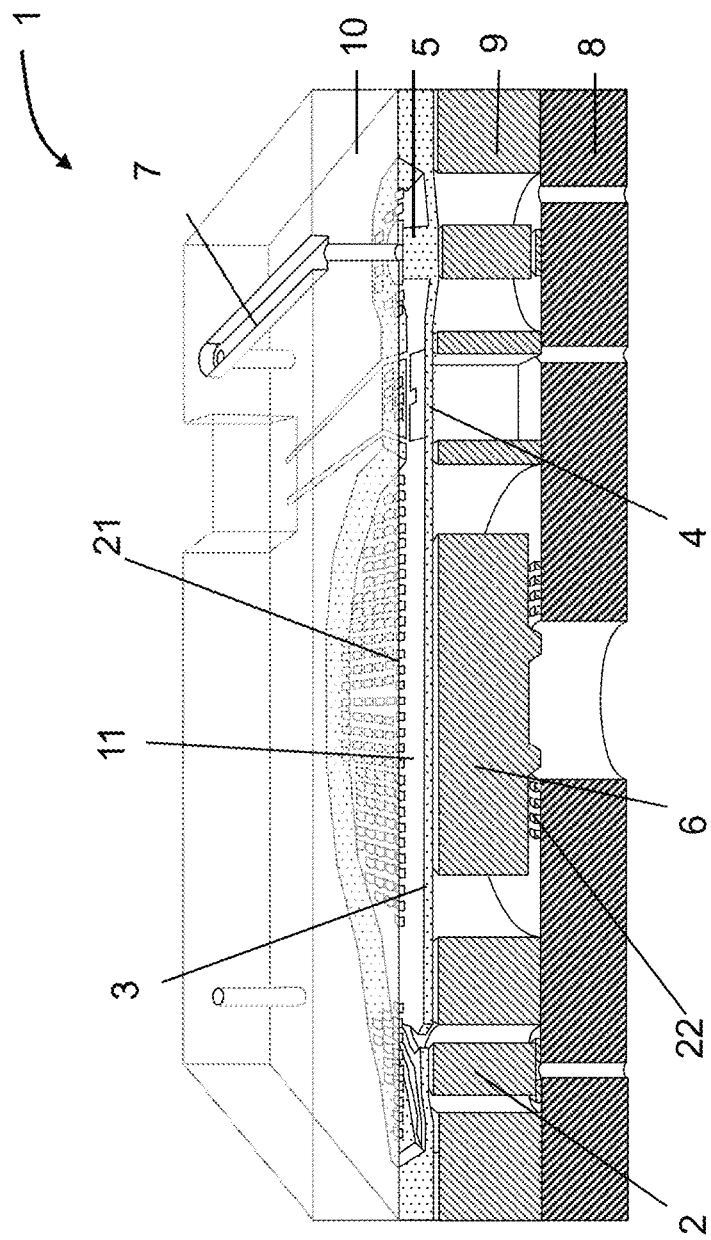
FIG. 1A shows a cross-hatched version of FIG. 1.
Figure 2:
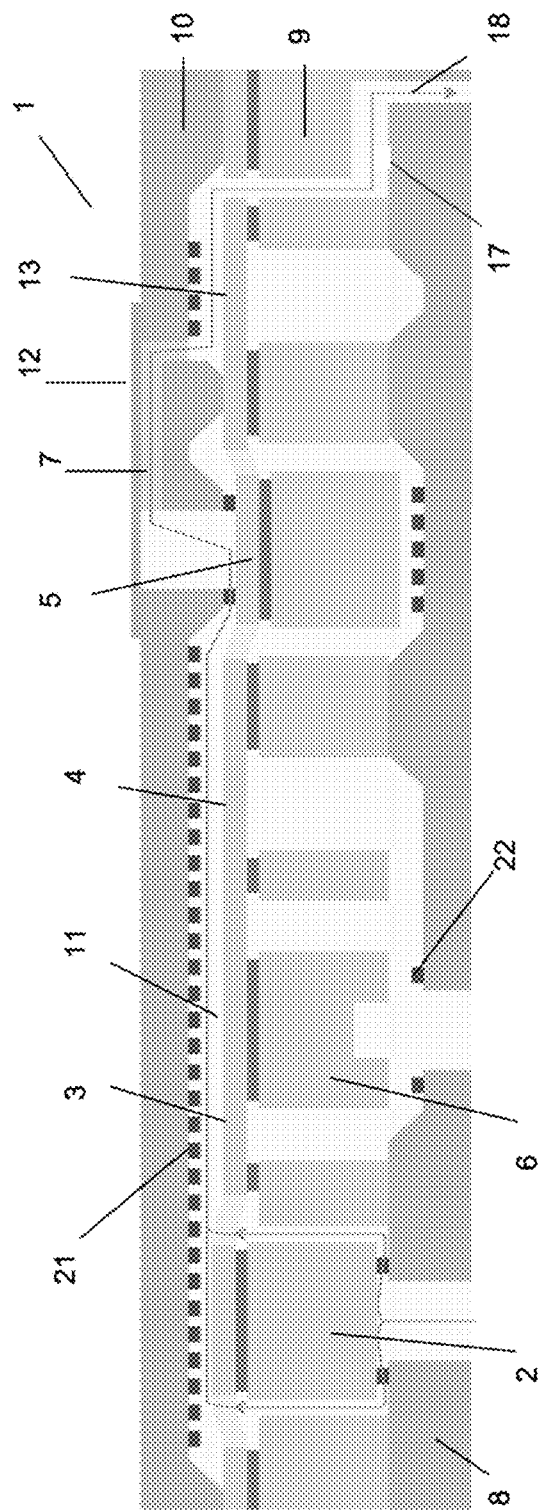
FIG. 2 shows the cross-section of the MEMS micropump including both detectors and showing the fluidic pathway
Figure 2A:
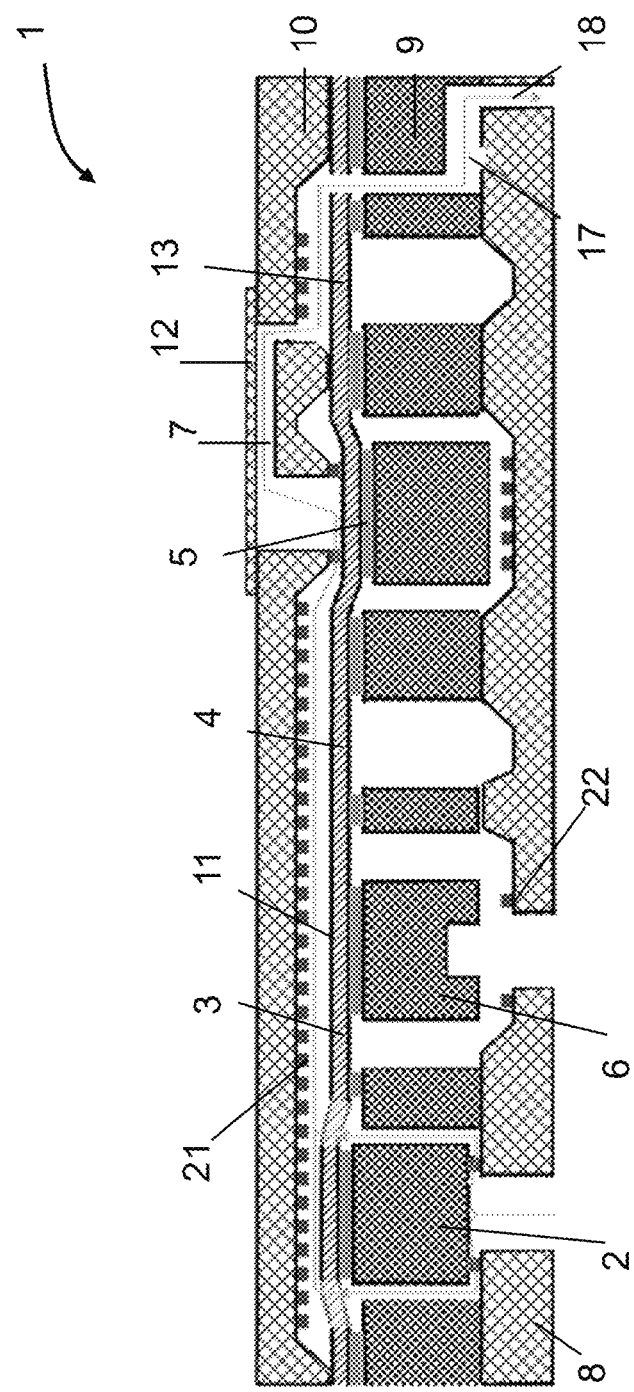
FIG. 2A shows a cross-hatched version of FIG. 2.
Figure 3:
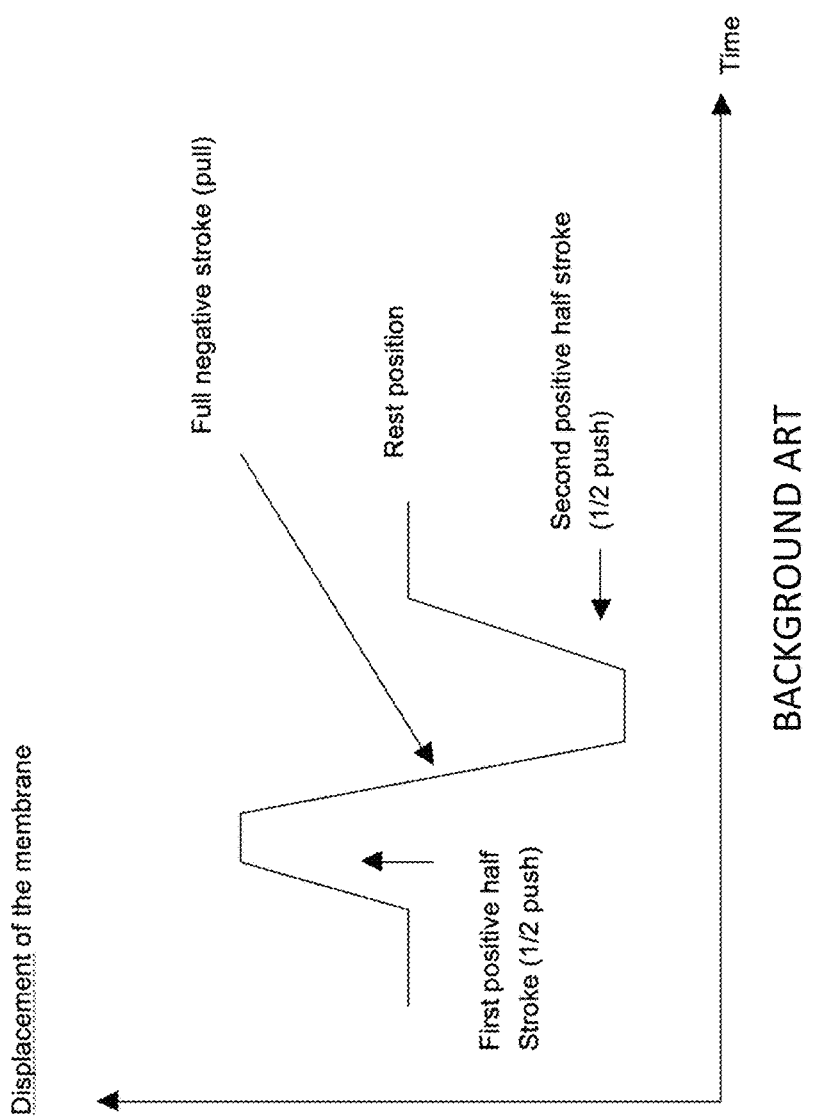
FIG. 3 shows a standard single shot actuation profile according to WO 2010/046728 for both basal and bolus modes.
Figure 4:
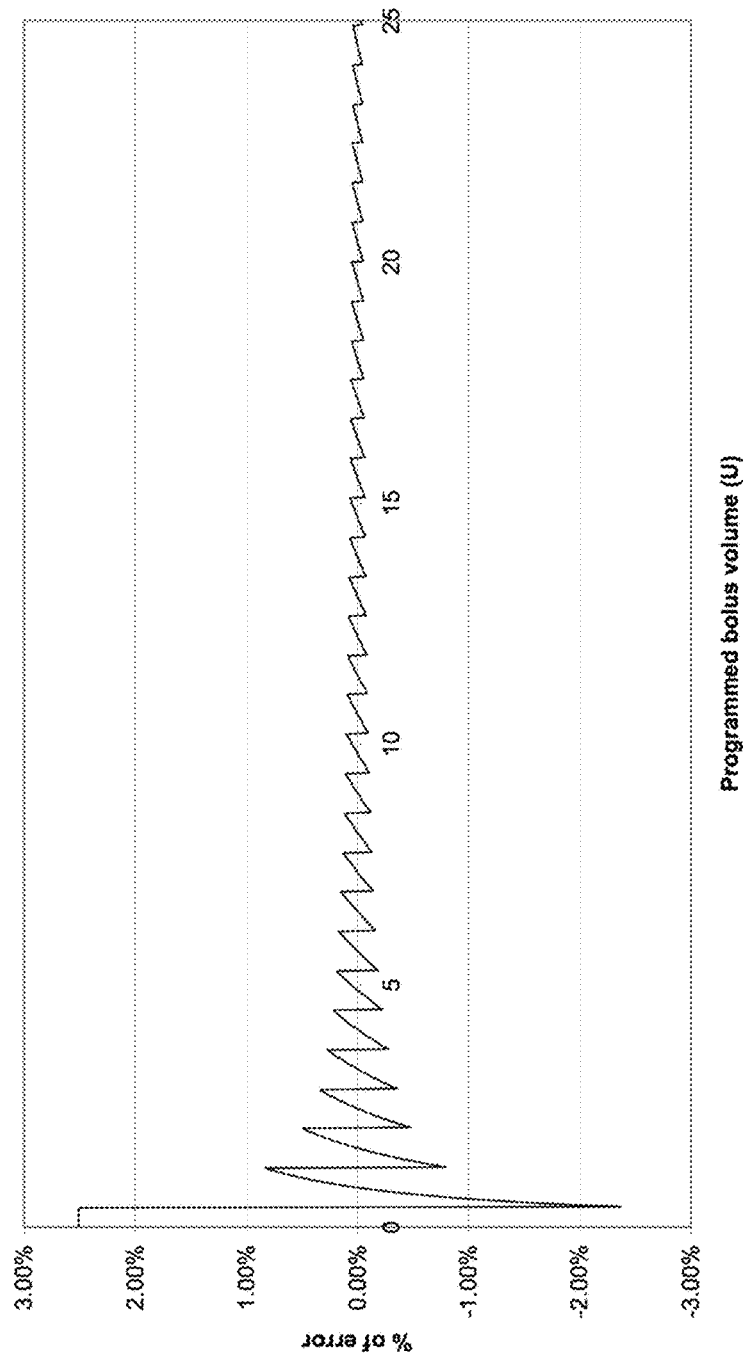
FIG. 4 is a graph of relative infusion error due to the bolus algorithm
Figure 5:
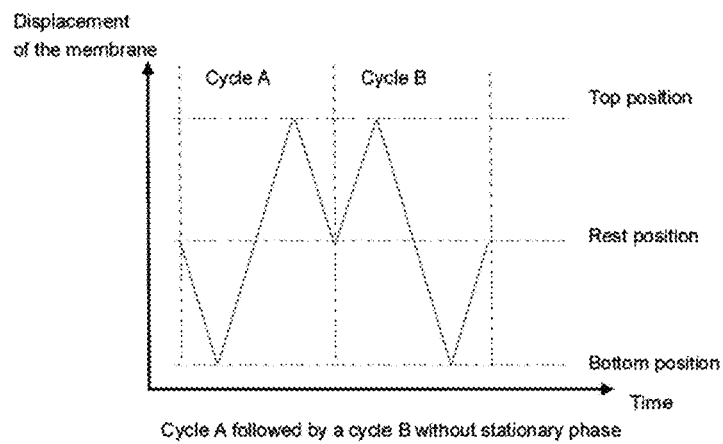
FIG. 5 shows different pumping pattern
Figure 5:
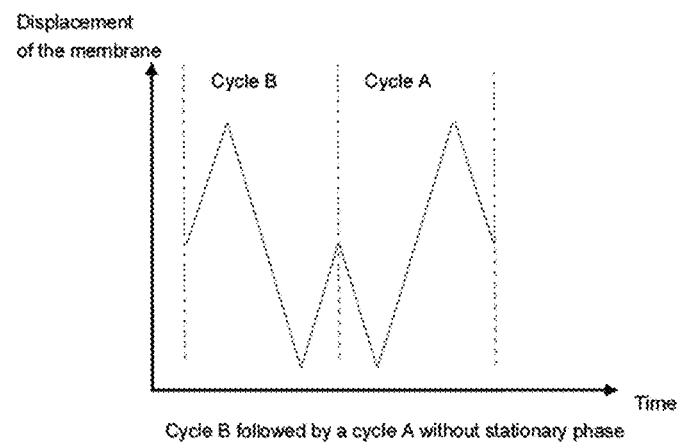
Figure 5:
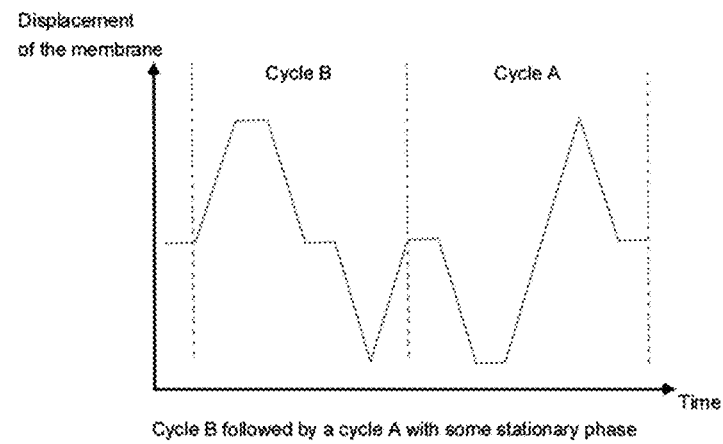

The max absolute error is equal to $$\frac{S_v(\text{bolus})}{2}$$

for any programmed $V_{bolus}$. There is no accumulated error. According to FIG. 4, the relative error as a function of the programmed bolus volume illustrates this feature.

To compensate the mismatch between the bolus stroke volume and the increment of bolus volume, a bolus algorithm is implemented and leads to a max relative error lower than +/−0.2% for bolus of 5 U or more.

The minimum bolus is equal to $S_V(\text{bolus})$ and therefore the max error for any bolus volume is equal to $+/-S_V(\text{bolus})/2$.

This bolus algorithm is a non-limiting example of the present invention.

Any other method using another rounding calculation, for any other nominal stroke volume can be used as bolus algorithm.

According to the methods described in the present invention, the pumping device should include means to compute the pumping pattern using nominal stroke volumes different for basal and bolus infusion.

The invention claimed is:

1. A method for actuating a pumping device by a pumping pattern to improve accuracy delivery, the pumping device including,
    a pumping chamber including a pumping membrane, a pressure sensor device, and an actuator connected to the membrane which is pushed by the actuator to generate a positive pressure of a fluid in the pumping chamber and is pulled by the actuator to generate a negative pressure,
    an inlet channel in fluid communication between a reservoir and the pumping chamber,
    an outlet channel in fluid communication between the pumping chamber and a patient line, and
    wherein the membrane is configured to be placed by the actuator to a rest position, a bottom position, and a top position, the rest position located between the bottom and the top positions,
    wherein the method includes the steps of:
    performing a number of cycles A of the pumping pattern; and
    performing a number of cycles B the pumping pattern,
    wherein the cycle A includes the steps of,
        (i) pushing the membrane towards the top position with the actuator to reach an upper position to perform a full-push or a partial-push;
        (ii) pulling the membrane from the upper position with the actuator to the rest position to perform a partial-pull, after the step (i); and
        (iii) resting the membrane at the rest position,
    wherein the cycle B includes the steps of,
        (iv) pulling the membrane towards the bottom position with the actuator to reach a lower position to perform a full-pull or a partial-pull;
        (v) pushing the membrane from the lower position with the actuator to the rest position to perform a partial-push, after the step (iv); and
        (vi) resting the membrane at the rest position
    wherein the number of cycles A and the number of cycles B of the pumping pattern are controlled based on a measurement from the pressure sensor device.

2. The method for actuating the pumping device according to claim 1,
    wherein a volume change of the pumping chamber is between 0.5 nL to 50 nL per bar of applied pressure when the pumping membrane is against a mechanical stop, and between 10 nL to 500 nL per bar of applied pressure when the pumping membrane is not against a mechanical stop and when the actuator is not powered.

3. The method for actuating the pumping device according to claim 1,
    wherein the inlet channel includes a first valve and the outlet channel includes a second valve, and wherein at least one of the first and second valves include a check valve.

4. The method for actuating the pumping device according to claim 1,
wherein the inlet channel includes a first valve and the outlet channel includes a second valve, and
wherein the first and the second valves have a pretension.

5. The method for actuating the pumping device according to claim 1, further comprising the step of:
performing a stationary phase in which the membrane is not moved by the actuator.

6. The method for actuating the pumping device according to claim 5,
wherein the inlet channel includes a first valve and the outlet channel includes a second valve, and
wherein during at least a part of the step of performing the stationary phase, the fluid flows through at least one of the first and the second valves.

7. The method according to claim 1, further comprising:
determining by the controller a ratio between a first fluidic resistance and a second fluidic resistance at the inlet channel and the outlet channel, respectively, based on the measurement of the pressure sensor device.

8. A method for actuating a pumping device with a pumping pattern to improve accuracy delivery, the pumping device including,
a pumping chamber including a pumping membrane, a pressure sensor device, and an actuator connected to the membrane which is pushed by the actuator to generate a positive pressure of a fluid in the pumping chamber and is pulled by the actuator to generate a negative pressure,
an inlet channel in fluid communication between a reservoir and the pumping chamber,
an outlet channel in fluid communication between the pumping chamber and a patient line, and
wherein the membrane is configured to be placed by the actuator to a rest position, a bottom position, and a top position,
wherein the method includes the steps of:
performing a number of pushing cycles of the pumping pattern; and
performing a number of pulling cycles of the pumping pattern,
wherein the pulling cycle includes the steps of,
(i) pulling the membrane with the actuator to reach the rest position; and
(ii) resting the membrane at the rest position, after the step (i), wherein the pushing cycle includes the steps of,
(iii) pushing the membrane with the actuator to reach the rest position; and
(iv) resting the membrane at the rest position, after the step (iii),
wherein the number of pushing cycles and the number of pulling cycles are controlled based on a measurement from the pressure sensor device.

9. The method for actuating the pumping device according to claim 8,
wherein a volume change of the pumping chamber is between 0.5 nL to 50 nL per bar of applied pressure when the pumping membrane is against a mechanical stop, and between 10 nL to 500 nL per bar of applied pressure when the pumping membrane is not against a mechanical stop and when the actuator is not powered.

10. The method for actuating the pumping device according to claim 8,
wherein the inlet channel includes a first valve and the outlet channel includes a second valve, and
wherein at least one of the first and the second valves includes a check valve.

11. The method for actuating the pumping device according to claim 8,
wherein the inlet channel includes a first valve and the outlet channel includes a second valve, and
wherein the first and second valves have a pretension.

12. The method for actuating the pumping device according to claim 8, further comprising the step of:
performing a stationary phase in which the membrane is not moved by the actuator.

13. The method for actuating the pumping device according to claim 12,
wherein the inlet channel includes a first valve and the outlet channel includes a second valve, and
wherein during at least a part of the step of performing the stationary phase, the fluid flows through at least one of the first and the second valves.

14. The method according to claim 8, further comprising:
determining by the controller a ratio between a first fluidic resistance and a second fluidic resistance at the inlet channel and the outlet channel, respectively, based on the measurement of the pressure sensor device.

15. A method for actuating a pumping device to improve accuracy delivery, the pumping device including,
a pumping chamber including a pumping membrane, a pressure sensor device, and an actuator connected to the membrane which is pushed by the actuator to generate a positive pressure of a fluid in the pumping chamber and is pulled by the actuator to generate a negative pressure,
an inlet channel and an outlet channel that are in fluidic communication with the pumping chamber, and
a controller operatively connected to the pressure sensor device and the actuator,
the method including the steps of:
controlling the actuator by the controller to perform a first number of pulling cycles by the membrane, the pulling cycles including (i) pulling the membrane to reach a rest position, and (ii) resting the membrane at the rest position, after (i); and
controlling the actuator by the controller to perform a second number of pushing cycles of the pumping pattern, the pushing cycles including (iii) pushing the membrane to reach the rest position, and (iv) resting the membrane at the rest position, after (iii),
wherein the first number of pushing cycles and the second number of pulling cycles are controlled based on a measurement from the pressure sensor device.

16. The method according to claim 15, further comprising:
determining a ratio between a first fluidic resistance and a second fluidic resistance at the inlet channel and the outlet channel, respectively, by the controller, based on the measurement of the pressure sensor device.

17. The method according to claim 16, wherein when the ratio is larger than 1, the first number of pushing cycles is larger than the second number of pulling cycles.

18. The method according to claim 16, wherein when the ratio is smaller than 1, the first number of pushing cycles is lower than the second number of pulling cycles.

19. The method according to claim 16, wherein when the ratio is 1, the first number of pushing cycles is equal to the second number of pulling cycles.

* * * * *